(12) United States Patent
Siengchum et al.

(10) Patent No.: US 11,982,604 B2
(45) Date of Patent: May 14, 2024

(54) QUANTIFICATION OF SURFACE ACIDITY ON A LOW SURFACE AREA MATERIAL

(71) Applicant: Saint-Gobain Ceramics & Plastics, Inc., Worcester, MA (US)

(72) Inventors: Tritti Siengchum, Peninsula, OH (US); James M Ralph, Copley, OH (US)

(73) Assignee: SAINT-GOBAIN CERAMICS & PLASTICS, INC., Worcester, MA (US)

( * ) Notice: Subject to any disclaimer, the term of this patent is extended or adjusted under 35 U.S.C. 154(b) by 306 days.

(21) Appl. No.: 17/309,002

(22) PCT Filed: Oct. 8, 2019

(86) PCT No.: PCT/US2019/055088
§ 371 (c)(1),
(2) Date: Apr. 9, 2021

(87) PCT Pub. No.: WO2020/076746
PCT Pub. Date: Apr. 16, 2020

(65) Prior Publication Data
US 2022/0026322 A1  Jan. 27, 2022

Related U.S. Application Data

(60) Provisional application No. 62/744,811, filed on Oct. 12, 2018.

(51) Int. Cl.
*G01N 1/40* (2006.01)
*F01N 11/00* (2006.01)
(Continued)

(52) U.S. Cl.
CPC ............ *G01N 1/405* (2013.01); *G01N 30/72* (2013.01); *G01N 33/0054* (2013.01);
(Continued)

(58) Field of Classification Search
CPC .... G01N 1/405; G01N 30/72; G01N 33/0054; G01N 33/388; G01N 2001/028; G01N 1/44; G01N 1/02; F01N 11/00
See application file for complete search history.

(56) References Cited

U.S. PATENT DOCUMENTS

2004/0141911 A1  7/2004  Cooper et al.
2007/0092974 A1*  4/2007  Swenson ............... G01N 15/088
436/164

(Continued)

FOREIGN PATENT DOCUMENTS

WO  2010/060648 A1  6/2010
WO  2015/001004 A1  1/2015

OTHER PUBLICATIONS

Niwa, Miki, et al. "Temperature-programmed desorption of ammonia with readsorption based on the derived theoretical equation." The Journal of Physical Chemistry 99.21 (1995): 8812-8816. (Year: 1995).*

(Continued)

*Primary Examiner* — Jill A Warden
*Assistant Examiner* — Michael Paul Shimek
(74) *Attorney, Agent, or Firm* — Abel Schillinger, LLP; Stewart A. Fraser; Thoburn Dunlap

(57) ABSTRACT

Methods and systems of analyzing and quantifying a surface acidity on a low surface area sample are disclosed. The methods include analyzing a quantity of an effluent molecular probe desorption from a temperature programmed desorption (TPD) process and system, by employing a mass spectroscopy (MS) system. The molecular probe is chemically adsorbed on a clean surface of the sample before the TPD process. The sample has a surface area to mass ratio of less than 5 m²/g. In some embodiments, the total surface area analyzed in the method can be as low as 3 m².

11 Claims, 4 Drawing Sheets

(51) Int. Cl.
  *G01N 1/02* (2006.01)
  *G01N 30/72* (2006.01)
  *G01N 33/00* (2006.01)
  *G01N 33/38* (2006.01)
(52) U.S. Cl.
  CPC ............ *G01N 33/388* (2013.01); *F01N 11/00* (2013.01); *G01N 2001/028* (2013.01)

(56) References Cited

U.S. PATENT DOCUMENTS

| | | | |
|---|---|---|---|
| 2007/0224081 | A1 | 9/2007 | Bokerman et al. |
| 2016/0220989 | A1 | 8/2016 | Elam et al. |
| 2018/0100107 | A1 | 4/2018 | Alhooshani et al. |
| 2018/0134647 | A1* | 5/2018 | Ozmeral .................. B01J 37/30 |

OTHER PUBLICATIONS

Schroeder, Sven LM, and Michael Gottfried. "Temperature-programmed desorption (TPD) thermal desorption spectroscopy (TDS)." Adv. Phys. Chem. Lab, FU Berlin, Jun. 2002 (2002). Accessed online Jun. 9, 2022. <http://pcprakt.userpage.fu-berlin.de/pdf_block_IV/TDS.pdf>. (Year: 2002).*

Shen, Yuesong, et al. "A novel catalyst of CeO2/Al2O3 for selective catalytic reduction of NO by NH3." Catalysis Communications 11.1 (2009): 20-23. (Year: 2009).*

Engtrakul, Chaiwat, et al. "Effect of ZSM-5 acidity on aromatic product selectivity during upgrading of pine pyrolysis vapors." Catalysis Today 269 (2016): 175-181. (Year: 2016).*

ASTM Intnl. "Standard Test Method for Determination of Low Surface Area of Catalysts and Catalyst Carriers by Multipoint Krypton Adsorption," Designation: D4780-12. (2017): 1-5. (Year: 2017).*

Deng, Hua, et al. "Palladium supported on low-surface-area fiber-based materials for catalytic oxidation of volatile organic compounds." Chemical Engineering Journal 348 (2018): 361-369. (Year: 2018).*

International Search Report from PCT Application No. PCT/US2019/055088 dated Jan. 31, 2020, 1 pg.

Francesco Arena et al: "An experimental assessment of ammonia temperature programmed desorption method for probing the surface acidic properties of heterogeneous catalysts", Applied Catalysis A: General, vol. 503, pp. 227-236, Available online Jun. 29, 2015.

Miki Niwa et al: "New Method for the Temperature-Programmed Desorption (TPD) of Ammonia Experiment for Characterization of Zeolite Acidity: A Review: TPD of Ammonia for Characterization of Zeolite Acidity", Chemical Record, vol. 13, No. 5, pp. 432-455; Available online Jul. 19, 2013.

* cited by examiner

QUANTIFICATION OF SURFACE ACIDITY ON A LOW SURFACE AREA MATERIAL

CROSS-REFERENCE TO RELATED APPLICATIONS

This application claims the benefit of U.S. Provisional Application No. 62/744,811 filed Oct. 12, 2018 and PCT/US2019/055088 filed Oct. 8, 2019.

TECHNICAL FIELD

The present disclosure relates generally to surface acidity analysis, and more particularly, to systems and methods for measuring surface acidity on a sample having a low surface area to mass ratio, for example, a surface area to mass ratio of less than 5 $m^2/g$.

BACKGROUND

Catalysts have broad applications in many of the important chemical or biochemical processes. Catalysts, in nature, are not designed to participate in a chemical reaction, but can change a chemical reaction rate by providing a different transition state and lower activation energy. Surface acidity is one of the important factors affecting catalytic performance. Therefore, quantification of surface acidity is a useful technique to determine the potential of any substrate in a catalytic reaction.

Surface acidity information can help to characterize catalyst carrier performance. For example, the diffusion of reagents and/or products to and from the surface can be rate determining. The surface properties of a catalyst carrier have important effects on the reaction rate of the catalytic process. The surface area of a catalyst carrier is intended to be inactive or inert but the presence of surface acidity can result in detrimental side reactions, lowering the overall catalyst performance. When the surface area is low for a given mass of a catalyst carrier (as characterized by a low surface area to mass ratio), the characterization of the surface acidity can be challenging.

Quantification of surface acidity on a substrate with a low surface area to mass ratio was not able to be performed using existing methods and systems because, when the surface area is limited, the amount of probe molecules used to characterize surface acidity that are absorbed on the substrate (which is proportional to the surface area) is very small. Typically, in such instances, the amount of probe molecules used to characterize surface acidity that are absorbed on the substrate is below the range that conventional equipment can measure accurately, for example, below 1 micromole per gram of catalyst carrier. In addition, pretreatment procedures for a surface acidity analysis can alter the properties of the substrate, which in turn, can impact the accuracy of the acidity analysis result. Furthermore, analysis of the desorbed probe molecules is required to be performed carefully to characterize the result, and because the low amount of the desorbed probe molecules from the low surface area, the result can be easily influenced by other unintended desorbed molecules.

As such, it would be desirable to provide a surface acidity quantification method and system that addresses the above-mentioned challenges.

SUMMARY

There is a need for an analysis technique that helps to address the shortcomings of conventional surface analysis methods and systems described above. In particular, there is a need for a surface acidity analysis that allows an accurate quantification of surface acidity on a surface of a substrate when the substrate has a surface area to mass ratio of less than 5 $m^2/g$. The quantification of surface acidity systems and methods described herein address these shortcomings by coupling temperature-programmed desorption (TPD) with analysis of effluent gases from TPD by mass spectroscopy (MS).

The analysis technique described herein can be commonly used for any ceramic material and other solid catalyst carriers. The understanding of the surface acidity on a surface having a low surface area to mass ratio can provide good evaluation for catalytic mechanisms and facilitate the design and development of new catalytic products.

According to one aspect of the invention described herein, a method of quantification of surface acidity of a sample includes the steps of: (1) removing surface moisture of the sample using a pretreatment process; (2) adsorbing a molecular probe on a surface of the sample; (3) removing physically adsorbed molecular probe from the surface of the sample; (4) releasing the adsorbed molecular probe by a method that includes a temperature programmed desorption (TPD) process; and (5) analyzing a total amount of the molecular probe desorbed from the TPD process by a method that includes mass spectroscopy (MS). And in some embodiments, the sample has a surface area to mass ratio of less than 5 $m^2/g$.

In some embodiments, the surface area to mass ratio is less than 1 $m^2/g$.

In some embodiments, the sample has a total surface area of at least 3 $m^2$.

In some embodiments, the sample has a total surface area of not greater than 25 $m^2$.

In some embodiments, the sample includes a catalyst carrier.

In some embodiments, the sample includes a ceramic material.

In some embodiments, the sample includes alumina, zirconia, titania, silica, zeolite, or a combination thereof.

In some embodiments, the method of quantification of surface acidity of a sample further includes: calculating a surface acidity site density based on the total amount of the molecular probe desorbed and a total surface area of the sample.

In some embodiments, the molecular probe is $NH_3$.

In some embodiments, the pretreatment process includes heating the sample for a predetermined duration within an inert gas flow.

In some embodiments, the pretreatment process includes heating the sample at about 6-10° C./min, from an initial temperature of about 50-100° C. to about 500-600° C., and maintaining a temperature of the sample of about 500-600° C. for about 15 to 30 minutes, and the sample is within a Helium or Argon gas flow at a flow rate of about 20-50 cm3/minute.

In some embodiments, the step of adsorbing a molecular probe further includes heating the sample for a predetermined duration within an inert gas flow mixed with the molecular probe.

In some embodiments, the step of adsorbing a molecular probe further includes maintaining a temperature of the sample of about 50-180° C. for about 10 to 20 minutes within a Helium or Argon gas mixed with 5% of the molecular probe flowing at a flow rate of about 10-50 $cm^3$/minute.

In some embodiments, the step of removing physically adsorbed molecular probe further includes heating the sample for a predetermined duration within an inert gas flow.

In some embodiments, the step of removing physically adsorbed molecular probe further includes maintaining a temperature of the sample of about 50-180° C. for about 60 to 120 minutes within a Helium or Argon gas flow at a flow rate of about 25-50 cm$^3$/minute.

In some embodiments, the TPD process further includes heating the sample with the molecular probe adsorption at gradually elevated temperatures for a predetermined duration within an inert gas flow.

In some embodiments, the TPD process further includes heating the sample with the molecular probe adsorption at about 6-10° C./min, from an initial temperature of about 50-100° C. to about 500-900° C., and maintaining a temperature of the sample of about 500-900° C. for about 15 to 30 minutes, and the sample is within a Helium or Argon gas flow at a flow rate of about 20-50 cm3/minute.

In some embodiments, the step of analyzing the total amount of the molecular probe further includes analyzing effluent gases that include the molecular probe desorbed from the TPD process.

In some embodiments, a type of molecular probe is determined based on a composition of the sample and a catalytic application of the sample.

In some embodiments, the molecular probe includes Pyridine or other alkaline molecule.

In some embodiments, the MS method includes using Quadrupole Mass Spectrometers.

In some embodiments, the MS method includes using a secondary electron multiplier detector.

According to another aspect of the invention described herein, a method of quantification of surface acidity on a sample with a low surface area to mass ratio, includes: analyzing, by a method that includes mass spectroscopy (MS), effluent molecular probe desorption from a process that includes a temperature programmed desorption (TPD). And in some embodiments, wherein the surface area to mass ratio of the sample is less than 5 m$^2$/g and the molecular probe is chemically adsorbed on a surface of the sample before the TPD process.

Note that the various embodiments described above can be combined with any other embodiments described herein. The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF THE DRAWINGS

The present disclosure may be better understood, and its numerous features and advantages made apparent to those skilled in the art by referencing the accompanying drawings. The accompanying drawings, however, merely illustrate pertinent features of the present disclosure and are therefore not to be considered limiting, for the description may admit to other effective features.

Figure 1:
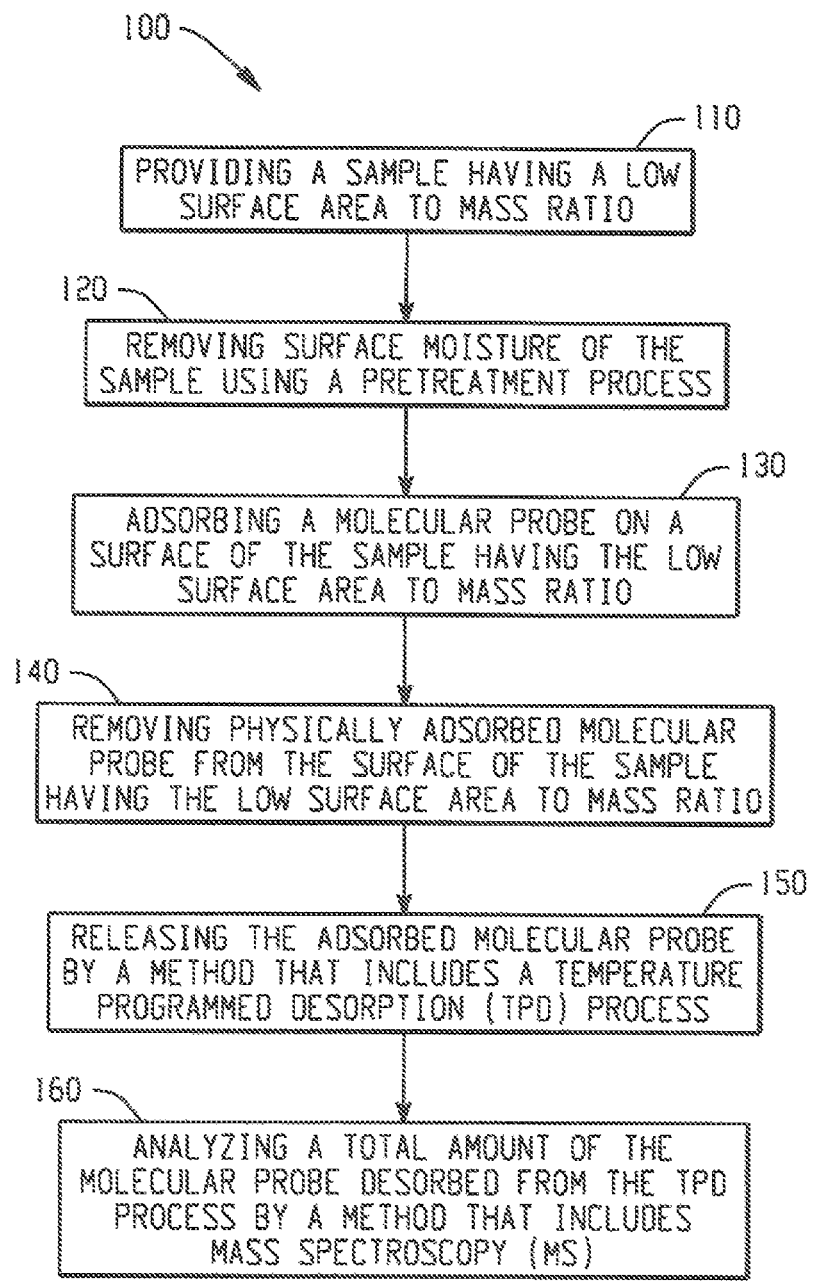
FIG. 1 shows a flow chart illustrating a process for surface acidity quantification on a low surface area of a sample, in accordance with some embodiments.

The use of the same reference symbols in different drawings indicates similar or identical items. In accordance with common practice, the various features illustrated in the drawings may not be drawn to scale. Accordingly, the dimensions of the various features may be arbitrarily expanded or reduced for clarity. In addition, some of the drawings may not depict all of the components of a given system, method or device.

DETAILED DESCRIPTION

Numerous details are described herein in order to provide a thorough understanding of the example embodiments illustrated in the accompanying drawings. However, some embodiments may be practiced without many of the specific details, and the scope of the claims is only limited by those features and aspects specifically recited in the claims. Furthermore, well-known processes, components, and materials have not been described in exhaustive detail so as not to unnecessarily obscure pertinent aspects of the embodiments described herein.

FIG. 1 shows a flow chart illustrating a process for surface acidity quantification on a low surface area according to embodiments described herein. As illustrated in FIG. 1, in some embodiments, a low surface area acidity quantification method 100 may include a step 110 of providing a sample having a low surface area to mass ratio; a step 120 of removing surface moisture of the sample using a pretreatment process; a step 130 of adsorbing a molecular probe on a surface of the sample having the low surface area to mass ratio; a step 140 of removing physically adsorbed molecular probe from the surface of the sample having the low surface area to mass ratio; a step 150 of releasing the adsorbed molecular probe by a method that includes a temperature programmed desorption (TPD) process; and a step 160 of analyzing a total amount of the molecular probe desorbed from the TPD process by a method that includes mass spectroscopy (MS).

According to some embodiments, the low surface area to mass ratio of the sample provided in step 110 has a surface area to mass ratio of less than 5 m$^2$/g, alternatively the surface area to mass ratio is less than 5 m$^2$/g and greater than 0.01 m$^2$/g. For example, the surface area to mass ratio can be less than 4 m$^2$/g, less than 3 m$^2$/g, less than 2 m$^2$/g, less than 1 m$^2$/g, or alternatively less than 0.5 m$^2$/g. Also for example, the sample having a low surface area to mass ratio provided in step 110 has a surface area to mass ratio of at least 0.01 m$^2$/g, at least 0.05 m$^2$/g, at least 0.1 m$^2$/g, at least 0.5 m$^2$/g, at least 1.0 m$^2$/g, at least 2.0 m$^2$/g, at least 3.0 m$^2$/g, at least 4.0 m$^2$/g, or alternatively at least 4.5 m$^2$/g. It will be appreciated that the sample may have a surface area to mass ratio of any value within a range between any of the minimum and maximum values noted above.

According to some embodiments, the sample with a low surface area to mass ratio provided in step 110 includes alumina. According to some embodiments, the sample with a low surface area to mass ratio provided in step 110 includes suitable ceramic materials such as alumina, zirconia, titania, silica, hafnia, or a combination thereof. According to some embodiments, the sample with a low surface area to mass ratio provided in step 110 includes suitable solid catalyst carrier materials, such as metal oxides, zeolites, graphic carbon, higher-order oxides, nanoparticles and surfaces of bulk materials or a combination thereof. According to some embodiments, the sample with a low surface area to mass ratio provided in step 110 includes suitable heterogeneous catalysts carrier materials. For example, most heterogeneous catalyst carriers are solids. In a catalytic reaction, the sample acts as a substrate in a liquid or gaseous reaction. The total surface area of the sample has an important effect on the reaction rate. The surface area of a sample catalyst generally has active sites where reaction actually occurs.

According to some embodiments, the total surface area of the sample is in the range of at least 2 $m^2$ to no greater than 25 $m^2$. For example, the total surface area can be at least 2 $m^2$, such as at least 3 $m^2$, at least 4 $m^2$, at least 5 $m^2$, at least 6 $m^2$, at least 7 $m^2$, at least 8 $m^2$, at least 9 $m^2$, at least 10 $m^2$, at least 12 $m^2$, at least 14 $m^2$, at least 16 $m^2$, at least 18 $m^2$, at least 20 $m^2$, at least 22 $m^2$, or even at least 24 $m^2$. According to some embodiments, the total surface area of the sample is no greater than 25 $m^2$, such as no greater than 24 $m^2$, no greater than 22 $m^2$, no greater than 20 $m^2$, no greater than 18 $m^2$, no greater than 16 $m^2$, no greater than 14 $m^2$, no greater than 12 $m^2$, no greater than 10 $m^2$, no greater than 9 $m^2$, no greater than 8 $m^2$, no greater than 7 $m^2$, no greater than 6 $m^2$, no greater than 5 $m^2$, or even no greater than 4 $m^2$. It will be appreciated that the sample may have a total surface area of any value within a range between any of the minimum and maximum values noted above.

In some embodiments, the sample is crushed and loaded into a reactor, such as a quartz reactor, in which some of the subsequent steps of the process 100 take place. In some embodiments, the reactor is placed into a furnace of a chemisorption analyzer, such as an Autochem II 2920 equipment. In some embodiments, the chemisorption analyzer can perform temperature-programmed desorption (TPD). In some embodiments, the chemisorption analyzer can also allow gases to flow through the surface area of the sample. In some embodiments, the chemisorption analyzer can detect the volume of the gas flowing through the sample reactor using a method, such as the thermal conductivity difference measurement between the gas and a reference gas. A furnace within the chemisorption analyzer chamber can be used to heat the sample reactor and the sample.

According to some embodiments, in the step 120 of removing surface moisture of the sample using a pretreatment process, the pretreatment process includes heating the sample for a predetermined duration within an inert gas flow. The purpose of pretreatment is to reduce an interference of other chemical such as water during the subsequent adsorption and desorption steps. In some embodiments, according to signals from MS, the pretreatment conditions can be optimized to achieve an acceptable signal to noise ratio, for example, a signal to noise ratio of greater than 100:1. In some embodiments, depending on the properties and quantity of the sample, during the pretreatment process of step 120, the sample is heated within the furnace at a target temperature after temperature elevation for a time period having a range of at least about 5 minutes to no longer than about 50 minutes. For example, the time period can be at least about 5 minutes, such as, at least about 10 minutes, at least about 15 minutes, at least about 20 minutes, at least about 25 minutes, at least about 30 minutes, at least about 35 minutes, at least about 40 minutes, or at least about 45 minutes. In some embodiments, depending on the properties and quantity of the sample, during the pretreatment process, the sample is heated within the furnace at a target temperature after temperature elevation for no longer than about 50 minutes, such as, no longer than about 45 minutes, no longer than about 40 minutes, no longer than about 35 minutes, no longer than about 30 minutes, no longer than about 25 minutes, no longer than about 20 minutes, no longer than about 15 minutes, or no longer than about 10 minutes. It will be appreciated that, during the pretreatment process, the sample may be heated within the furnace at a target temperature after temperature elevation for any time value within a range between any of the minimum and maximum values noted above. It will be further appreciated that, during the pretreatment process, the sample may be heated within the furnace for any time value suitable to remove substantially all surface moisture.

In some embodiments, depending on the properties and quantity of the sample, during the pretreatment process of step 120, the sample is heated within the furnace from an initial temperature, for example, 50° C., to a temperature with a range of at least about 250° C. to no greater than about 850° C. For example, the temperature to which the sample is heated can be at least about 250° C., such as, at least about 300° C., at least about 350° C., at least about 400° C., at least about 450° C., at least about 500° C., at least about 550° C., at least about 600° C., at least about 650° C., at least about 700° C., at least about 750° C., at least about 800° C., or at least about 850° C. In some embodiments, depending on the properties and quantity of the sample, during the pretreatment process, the temperature to which the sample is heated within the furnace can be from an initial temperature, for example, 50° C., to no greater than about 850° C., such as, no greater than about 800° C., no greater than about 750° C., no greater than about 700° C., no greater than about 650° C., no greater than about 600° C., no greater than about 550° C., no greater than about 500° C., no greater than about 450° C., no greater than about 400° C., no greater than about 350° C., no greater than about 300° C., or no greater than about 250° C. It will be appreciated that, during the pretreatment process, the sample may be heated within the furnace to any temperature value within a range between any of the minimum and maximum values noted above.

In some embodiments, depending on the properties and quantity of the sample, during the pretreatment process of step 120, the sample is heated in the furnace within an inert gas, such as a Helium or Argon gas.

In some embodiments, depending on the properties and quantity of the sample, during the pretreatment process of step 120, the sample is heated within the furnace at a heating rate having a range of at least about 3° C./min to no greater than about 20° C./min from an initial temperature, for example, 50° C. In some embodiments, depending on the properties and quantity of the sample, the heating rate is at least about 2° C./min from an initial temperature, for example, 50° C., such as, at least about 3° C./min, at least about 4° C./min, at least about 5° C./min, at least about 6° C./min, at least about 7° C./min, at least about 8° C./min, at least about 9° C./min, at least about 10° C./min, at least about 12° C./min, at least about 14° C./min, at least about 16° C./min, at least about 18° C./min, or at least about 20° C./min. In some embodiments, depending on the properties and quantity of the sample, during the pretreatment process of step 120, the heating rate is no greater than about 20° C./min from an initial temperature, for example, 50° C., such as, no greater than about 18° C./min, no greater than about 16° C./min, no greater than about 14° C./min, no greater than about 12° C./min, no greater than about 10° C./min, no greater than about 9° C./min, no greater than about 8° C./min, no greater than about 7° C./min, no greater than about 6° C./min, no greater than about 5° C./min, no greater than about 4° C./min, no greater than about 3° C./min, or no greater than about 2° C./min. It will be appreciated that, during the pretreatment process, the sample may be heated within the furnace at a heating rate value within a range between any of the minimum and maximum values noted above.

In some embodiments, depending on the properties and quantity of the sample, during the pretreatment process of step 120, the flow rate of the inert gas through or across the surface of the sample is within a range of at least about 5 $cm^3$/minute to no greater than about 55 $cm^3$/minute. In some embodiments, depending on the properties and quantity of the sample, the flow rate of the inert gas through or across the surface of the sample is at least about 5 $cm^3$/minute, such as, at least about 10 $cm^3$/minute, at least about 15 $cm^3$/minute, at least about 20 $cm^3$/minute, at least about 25 $cm^3$/minute, at least about 30 $cm^3$/minute, at least about 35 $cm^3$/minute, at least about 40 $cm^3$/minute, at least about 45 $cm^3$/minute, or at least about 55 $cm^3$/minute. In some embodiments, depending on the properties and quantity of the sample, during the pretreatment process of step 120, the flow rate of the inert gas through the surface of the sample is no greater than about 55 $cm^3$/minute, such as, no greater than about 50 $cm^3$/minute, no greater than about 45 $cm^3$/minute, no greater than about 40 $cm^3$/minute, no greater than about 35 $cm^3$/minute, no greater than about 30 $cm^3$/minute, no greater than about 25 $cm^3$/minute, no greater than about 20 $cm^3$/minute, no greater than about 15 $cm^3$/minute, no greater than about 10 $cm^3$/minute, or no greater than about 5 $cm^3$/minute. It will be appreciated that, during the pretreatment process, the flow rate of the inert gas through the surface of the sample has a value within a range between any of the minimum and maximum values noted above.

In some other embodiments, the method of removing surface moisture from the sample includes other methods such as cleaning the surface of the sample using a chemical method, such as using chemical solutions. In yet some other embodiments, the method of removing surface moisture from the sample includes other methods such as cleaning the surface of the sample using a mechanical method.

According to some embodiments, in the step 130 of adsorbing a molecular probe on a surface of the sample having the low surface area to mass ratio, a probe molecule is chosen based on the composition and catalytic application of the sample. In some embodiments, Ammonia (NH3) is selected as a probe molecule. In some embodiments, Pyridine (C5H5N) or other basic compound is selected as a probe molecule. In some embodiments, an alkaline molecule is selected as a probe molecule. In some embodiments, N-butylamine, Acetone, Acetonitrile, Ethylene, Trimethylphosphine, or Trimethyl-phosphine oxide probe molecules can be used with any type of sample depending on the purpose of study and equipment available in a lab.

In some embodiments, the adsorption step 130 includes heating the sample for a predetermined duration within an inert gas flow mixed with the molecular probe. In some embodiments, depending on the properties and quantity of the sample, during the adsorption step 130, the sample is heated within the furnace for a time period having a range of at least about 5 minutes to no longer than about 45 minutes. In some embodiments, depending on the properties and quantity of the sample, during the adsorption step 130, the sample is heated within the furnace for at least about 5 minutes, such as, at least about 10 minutes, at least about 15 minutes, at least about 20 minutes, at least about 25 minutes, at least about 30 minutes, at least about 35 minutes, or at least about 40 minutes. In some embodiments, depending on the properties and quantity of the sample, during the adsorption step 130, the sample is heated within the furnace for no longer than about 45 minutes, such as, no longer than about 40 minutes, no longer than about 35 minutes, no longer than about 30 minutes, no longer than about 25 minutes, no longer than about 20 minutes, no longer than about 15 minutes, no longer than about 10 minutes, or no longer than about 5 minutes. It will be appreciated that, during the adsorption step 130, the sample may be heated within the furnace for any time value within a range between any of the minimum and maximum values noted above.

In some embodiments, depending on the properties and quantity of the sample, during the adsorption step 130, the sample is heated within the furnace at a temperature having a range of at least about 20° C. and no greater than 300° C. In some embodiments, depending on the properties and quantity of the sample, during the adsorption step 130, the sample is heated within the furnace at a temperature of at least about 20° C., such as, at least about 30° C., at least about 40° C., at least about 50° C., at least about 60° C., at least about 70° C., at least about 80° C., at least about 90° C., at least about 100° C., at least about 120° C., at least about 140° C., at least about 160° C., at least about 180° C., or at least about 200° C. In some embodiments, depending on the properties and quantity of the sample, during the adsorption step 130, the sample is heated within the furnace at a temperature of no greater than about 300° C., such as, no greater than about 270° C., no greater than about 240° C., no greater than about 210° C., no greater than about 180° C., no greater than about 150° C., no greater than about 120° C., no greater than about 90° C., no greater than about 80° C., no greater than about 70° C., no greater than about 60° C., or no greater than about 50° C. It will be appreciated that, during the adsorption step 130, the sample may be heated within the furnace at any temperature value within a range between any of the minimum and maximum values noted above.

In some embodiments, depending on the properties and quantity of the sample, during the adsorption step 130, the sample is heated in the furnace within an inert gas, such as a Helium gas or Argon gas. Nitrogen (N2) gas is not recommended due to the ability to adsorb on strong acid sites.

In some embodiments, the gas mixture flowing through or across the surface of the sample, during the adsorption step 130, includes a gas mixture range of at least 1% and no greater than 20% of the probe molecule gas by volume. In some embodiments, the gas mixture flowing through the surface of the sample, during the adsorption step 130, includes at least 1% of the probe molecule gas by volume, such as, at least 2% of the probe molecule gas, at least 3% of the probe molecule gas, at least 4% of the probe molecule gas, at least 5% of the probe molecule gas, at least 7% of the probe molecule gas, at least 9% of the probe molecule gas, at least 11% of the probe molecule gas, at least 13% of the probe molecule gas, or at least 15% of the probe molecule gas. In some embodiments, the gas mixture flowing through the surface of the sample, during the adsorption step 130, includes no greater than 20% of the probe molecule gas by volume, such as, no greater than 15% of the probe molecule gas, no greater than 10% of the probe molecule gas, no greater than 8% of the probe molecule gas, no greater than 6% of the probe molecule gas, no greater than 4% of the probe molecule gas, or no greater than 2% of the probe molecule gas. It will be appreciated that, during the adsorption step 130, the percentage of the probe molecule gas in the gas flow has any value within a range between any of the minimum and maximum values noted above.

In some embodiments, depending on the properties and quantity of the sample, during the adsorption step 130, the flow rate of the gas mixture through or across the surface of the sample has a range of at least about 5 $cm^3$/minute and no greater than about 40 $cm^3$/minute. In some embodiments, depending on the properties and quantity of the sample, during the adsorption step 130, the flow rate of the gas mixture through the surface of the sample is at least about 5 $cm^3$/minute, such as, at least about 10 $cm^3$/minute, at least about 15 $cm^3$/minute, at least about 20 $cm^3$/minute, at least about 25 $cm^3$/minute, at least about 30 $cm^3$/minute, at least about 35 $cm^3$/minute, or at least about 40 $cm^3$/minute. In some embodiments, depending on the properties and quantity of the sample, during the adsorption step 130, the flow rate of the gas mixture, through the surface of the sample is no greater than about 40 $cm^3$/minute, such as, no greater than about 35 $cm^3$/minute, no greater than about 30 $cm^3$/minute, no greater than about 25 $cm^3$/minute, no greater than about 20 $cm^3$/minute, no greater than about 15 $cm^3$/minute, no greater than about 10 $cm^3$/minute, or no greater than about 5 $cm^3$/minute. It will be appreciated that, during the pretreatment process, the flow rate of the inert gas through the surface of the sample has a value within a range between any of the minimum and maximum values noted above.

During a chemical adsorption process, electrons are shared between the probe molecule gas and certain solid surfaces of the sample to form a chemical bond. Generally, chemical adsorption forms a single layer on a surface. The chemical adsorption stops when the probe molecule can no longer contact directly with the surface of the sample. Under suitable temperature and pressure, physical adsorption also takes place on all surfaces of the sample and can form layers beyond the single layer of chemical adsorption.

According to some embodiments, in the step 140 of removing physically adsorbed molecular probe from the surface of the sample having the low surface area to mass ratio, a flushing process is used. The flushing process includes heating the sample for a predetermined duration within an inert gas flow. Generally, only chemically adsorbed probe molecules are useful in the analysis of determining active sites of the surface area of sample. The flushing process can be used to remove physically adsorbed probe molecules as described above.

In some embodiments, depending on the properties and quantity of the sample, during the flushing process of step 140, the sample is heated within the furnace for a period of time. For example, the period of time can be from at least about 40 minutes to no longer than about 140 minutes. For example, the period of time can be at least about 40 minutes, such as, at least about 50 minutes, at least about 60 minutes, at least about 70 minutes, at least about 80 minutes, at least about 90 minutes, at least about 100 minutes, at least about 110 minutes, at least about 120 minutes, at least about 130 minutes, or at least about 140 minutes. In some embodiments, depending on the properties and quantity of the sample, during the flushing process of step 140, the sample is heated within the furnace for no longer than about 140 minutes, such as, no longer than about 130 minutes, no longer than about 120 minutes, no longer than about 110 minutes, no longer than about 100 minutes, no longer than about 90 minutes, no longer than about 80 minutes, no longer than about 70 minutes, no longer than about 60 minutes, no longer than about 50 minutes, or no longer than about 40 minutes. It will be appreciated that, during the flushing process of step 140, the sample may be heated within the furnace for any time value within a range between any of the minimum and maximum values noted above.

In some embodiments, depending on the properties and quantity of the sample, during the flushing process of step 140, the sample is heated within the furnace at a temperature range of at least about 20° C. and no greater than about 300° C. In some embodiments, depending on the properties and quantity of the sample, during the flushing process of step 140, the sample is heated within the furnace at a temperature of at least about 20° C., such as, at least about 30° C., at least about 40° C., at least about 50° C., at least about 60° C., at least about 70° C., at least about 80° C., at least about 90° C., at least about 100° C., at least about 120° C., at least about 140° C., at least about 160° C., at least about 180° C., or at least about 200° C. In some embodiments, depending on the properties and quantity of the sample, the flushing process of step 140, the sample is heated within the furnace at a temperature of no greater than about 300° C., such as, no greater than about 270° C., no greater than about 240° C., no greater than about 210° C., no greater than about 180° C., no greater than about 150° C., no greater than about 120° C., no greater than about 90° C., no greater than about 80° C., no greater than about 70° C., no greater than about 60° C., or no greater than about 50° C. It will be appreciated that, the flushing process of step 140, the sample may be heated within the furnace at any temperature value within a range between any of the minimum and maximum values noted above.

In some embodiments, depending on the properties and quantity of the sample, during the flushing process of step 140, the sample is heated in the furnace within an inert gas, such as a Helium or Argon gas.

In some embodiments, depending on the properties and quantity of the sample, during the flushing process of step 140, the flow rate of the inert gas through or across the surface of the sample is at least about 5 cm3/minute and no greater than about 100 cm3/minute. In some embodiments, depending on the properties and quantity of the sample, during the flushing process of step 140, the flow rate of the inert gas through the surface of the sample is at least about 5 cm3/minute, such as, at least about 10 cm3/minute, at least about 15 cm3/minute, at least about 20 cm3/minute, at least about 30 cm3/minute, at least about 40 cm3/minute, at least about 50 cm3/minute, at least about 60 cm3/minute, at least about 70 cm3/minute, or at least about 100 cm3/minute. In some embodiments, depending on the properties and quantity of the sample, during the flushing process of step 140, the flow rate of the inert gas through the surface of the sample is no greater than about 100 cm3/minute, such as, no greater than about 70 cm3/minute, no greater than about 60 cm3/minute, no greater than about 50 cm3/minute, no greater than about 40 cm3/minute, no greater than about 30 cm3/minute, no greater than about 20 cm3/minute, no greater than about 15 cm3/minute, no greater than about 10 cm3/minute, or no greater than about 5 cm3/minute. It will be appreciated that, the flushing process of step 140, the flow rate of the inert gas through the surface of the sample has a value within a range between any of the minimum and maximum values noted above.

In some other embodiments, Step 140 of removing physically adsorbed molecular probe from the low surface area of the sample can be accomplished using other mechanical or chemical methods.

According to some embodiments, in the step 150 of releasing the adsorbed molecular probe by a method that includes a temperature programmed desorption (TPD) process, the TPD process includes heating the sample with the molecular probe adsorption at continuously elevated temperatures for a predetermined duration within an inert gas flow.

In some embodiments, during the TPD process of step 150, the temperature for heating the sample within the furnace was increased continuously with time, for example, linearly with time, from an initial temperature, for example, 50° C., to a target temperature in a controlled manner. In some embodiments, depending on the properties and quantity of the sample, during the TPD process of step 150, the sample is heated within the furnace from an initial temperature, for example, 50° C., to at a temperature range of least about 250° C. and no greater than about 1500° C. In some embodiments, depending on the properties and quantity of the sample, during the TPD process of step 150, the sample is heated within the furnace from an initial temperature, for example, 50° C., to at a temperature of least about 250° C., such as, at least about 300° C., at least about 350° C., at least about 400° C., at least about 450° C., at least about 500° C., at least about 550° C., at least about 600° C., at least about 650° C., at least about 700° C., at least about 750° C., at least about 800° C., at least about 850° C., at least about 900° C., at least about 1000° C., at least about 1200° C., or at least about 1500° C. In some embodiments, depending on the properties and quantity of the sample, during the TPD process of step 150, the sample is heated within the furnace from an initial temperature, for example, 50° C., to no greater than about 1500° C., such as, no greater than about 1200° C., no greater than about 1000° C., no greater than about 900° C., no greater than about 850° C., no greater than about 800° C., no greater than about 750° C., no greater than about 700° C., no greater than about 650° C., no greater than about 600° C., no greater than about 550° C., no greater than about 500° C., no greater than about 450° C., no greater than about 400° C., no greater than about 350° C., no greater than about 300° C., or no greater than about 250° C. It will be appreciated that, during the TPD process of step 150, the sample may be heated within the furnace to any temperature value within a range between any of the minimum and maximum values noted above.

In some embodiments, depending on the properties and quantity of the sample, during the TPD process of step 150, the sample is heated in the furnace within an inert gas, such as a Helium or Argon gas.

In some embodiments, depending on the properties and quantity of the sample, during the TPD process of step 150, the heating rate is at least about 2° C./min and no greater than 20° C./min from an initial temperature, for example, 50° C. In some embodiments, depending on the properties and quantity of the sample, during the TPD process of step 150, the heating rate is at least about 2° C./min from an initial temperature, for example, 50° C., such as, at least about 3° C./min, at least about 4° C./min, at least about 5° C./min, at least about 6° C./min, at least about 7° C./min, at least about 8° C./min, at least about 9° C./min, at least about 10° C./min, at least about 12° C./min, at least about 14° C./min, at least about 16° C./min, at least about 18° C./min, or at least about 20° C./min. In some embodiments, depending on the properties and quantity of the sample, during the TPD process of step 150, the heating rate is no greater than about 20° C./min from an initial temperature, for example, 50° C., such as, no greater than about 18° C./min, no greater than about 16° C./min, no greater than about 14° C./min, no greater than about 12° C./min, no greater than about 10° C./min, no greater than about 9° C./min, no greater than about 8° C./min, no greater than about 7° C./min, no greater than about 6° C./min, no greater than about 5° C./min, no greater than about 4° C./min, no greater than about 3° C./min, or no greater than about 2° C./min. It will be appreciated that, during the TPD process of step 150, the sample may be heated within the furnace at a heating rate value within a range between any of the minimum and maximum values noted above.

In some embodiments, depending on the properties and quantity of the sample, during the TPD process of step 150, the sample is heated within the furnace at a target temperature after temperature elevation for a period of time of at least about 5 minutes and no longer than about 120 minutes. In some embodiments, depending on the properties and quantity of the sample, during the TPD process of step 150, the sample is heated within the furnace at a target temperature after temperature elevation for a period of time of at least about 5 minutes, such as, at least about 10 minutes, at least about 15 minutes, at least about 20 minutes, at least about 25 minutes, at least about 30 minutes, at least about 35 minutes, at least about 40 minutes, at least about 50 minutes, at least about 60 minutes, at least about 90 minutes, or at least about 120 minutes. In some embodiments, depending on the properties and quantity of the sample, during the TPD process of step 150, the sample is heated within the furnace at a target temperature after temperature elevation for no longer than about 120 minutes, such as, no longer than about 100 minutes, no longer than about 80 minutes, no longer than about 60 minutes, no longer than about 50 minutes, no longer than about 45 minutes, no longer than about 40 minutes, no longer than about 35 minutes, no longer than about 30 minutes, no longer than about 25 minutes, no longer than about 20 minutes, no longer than about 15 minutes, no longer than about 10 minutes, or no longer than about 5 minutes. It will be appreciated that, during the TPD process of step 150, the sample may be heated within the furnace at a target temperature after temperature elevation for any time value within a range between any of the minimum and maximum values noted above.

In some embodiments, depending on the properties and quantity of the sample, during the TPD process of step 150, the flow rate of the inert gas through or across the surface of the sample is at least about 5 $cm^3$/minute and no greater than about 55 $cm^3$/minute. In some embodiments, depending on the properties and quantity of the sample, during the TPD process of step 150, the flow rate of the inert gas through the surface of the sample is at least about 5 $cm^3$/minute, such as, at least about 10 $cm^3$/minute, at least about 15 $cm^3$/minute, at least about 20 $cm^3$/minute, at least about 25 $cm^3$/minute, at least about 30 $cm^3$/minute, at least about 35 $cm^3$/minute, at least about 40 $cm^3$/minute, at least about 45 $cm^3$/minute, or at least about 55 $cm^3$/minute. In some embodiments, depending on the properties and quantity of the sample, during the TPD process of step 150, the flow rate of the inert gas through the surface of the sample is no greater than about 55 $cm^3$/minute, such as, no greater than about 50 $cm^3$/minute, no greater than about 45 $cm^3$/minute, no greater than about 40 $cm^3$/minute, no greater than about 35 $cm^3$/minute, no greater than about 30 $cm^3$/minute, no greater than about 25 $cm^3$/minute, no greater than about 20 $cm^3$/minute, no greater than about 15 $cm^3$/minute, no greater than about 10 $cm^3$/minute, or no greater than about 5 $cm^3$/minute. It will be appreciated that, during the TPD process of step 150, the flow rate of the inert gas through the surface of the sample has a value within a range between any of the minimum and maximum values noted above.

In some embodiments, during the TPD process of step 150, the chemically adsorbed probe molecules are released from the surface area of sample and turned back to their gas phase.

In some other embodiments, releasing the adsorbed molecular probe can be implemented using other suitable desorption methods such as Temperature Programmed Reaction.

According to some embodiments, the step 160 of analyzing a total amount of the molecular probe desorbed from the TPD process by a method that includes mass spectroscopy (MS), the MS is coupled to the TPD apparatus including the chemisorption analyzer. In some embodiments, the step 140 and step 150 are carried out substantially simultaneously.

In some embodiments, the MS used is a Quadrupole Mass Spectrometer. In some embodiments, a filter system of the Quadrupole Mass Spectrometer creates a radio frequency (RF) quadrupole oscillating electrical field by four parallel rods arranged in the form of a square. The electrical field selectively stabilizes or destabilizes the paths of ions passing through the field between the four parallel rods. The potentials on the four rods can be changed continuously or discretely to allow ions in a certain range of mass/charge ratio (m/z) to pass through the system.

In some embodiments, the Quadrupole Mass Spectrometer is equipped with one or more secondary electron multiplier (SEM) detectors. In some embodiments, the combination of Quadrupole Mass Spectrometer with an SEM detector can improve the performance of the MS in terms of sensitivity and selectivity compared with conventional methods and systems. For example, in some conventional methods, a thermal conductivity detector (TCD) is used to measure the quantity of the probe molecules, which leads to low resolution and inaccuracy.

In some embodiments, the gas released in step 140 containing the probe molecules is ionized by the MS. In some embodiments, the gas is ionized by bombarding the gas with electrons. In some embodiments, the gas molecules are broken into charge fragments. In some embodiments, those ions are separated by their mass-to charge ratio (m/z) and detected by the SEM detectors.

In some embodiments, the MS is further controlled by a computer that monitors the effluent gas from the TPD process in step 140. In some embodiments, the computer analyzes the results of MS automatically.

In some embodiments, the desorbed probe molecules from the TPD process in step 140 are ionized and measured by the MS. In some embodiments, the MS can report a relative abundance of detected ions of each species in the gas from the TPD process as a function of a mass to charge ratio (m/z).

In some embodiments, the result signals obtained from MS are then calibrated and converted into the concentration profile and/or temperature profile of the probe molecule as a function of time recorded from the start of the TPD process of step 140. In some embodiments, the remaining gas from the TPD and MS processes is removed through a vent.

In some embodiments, from the probe molecule desorption profile and the temperature profile generated by MS in step 150, the effluent flow rate of the probe molecule from TPD process initially increases as the temperature increases. In some embodiments, the effluent probe molecule flow rate reaches a peak at about $1 \times 10^{-3}$ to $1 \times 10-4$ cm$^3$/min in about 5-40 minutes from the start of the TPD process in step 140. In some embodiments, the effluent flow rate of the probe molecule starts to decrease as the temperature continues to increase in the TPD process of step 140.

In some embodiments, after about 60 minutes to 120 minutes in the TPD process, the temperature stabilizes at about one temperature value within about 250° C.-1500° C. while the effluent flow rate of the probe molecule decreases to a negligible level of below about $5 \times 10^{-4}$ to $1 \times 10^{-3}$ cm$^3$/min.

In some embodiments, the desorption curve or concentration profile of the probe molecule is further integrated to obtain a total amount of the probe molecule adsorption from the low surface of the sample. In some embodiments, with known total surface area of the sample in step 110, the surface acidity site density can be calculated to characterize the surface acidity of the sample, for example, using a mass balance equation.

Further embodiments also include various subsets of the above embodiments, for example, including any of the variations of time, temperature, heating rate, gas composition, and gas flow rate combined or otherwise re-arranged in various embodiments.

Figure 2:
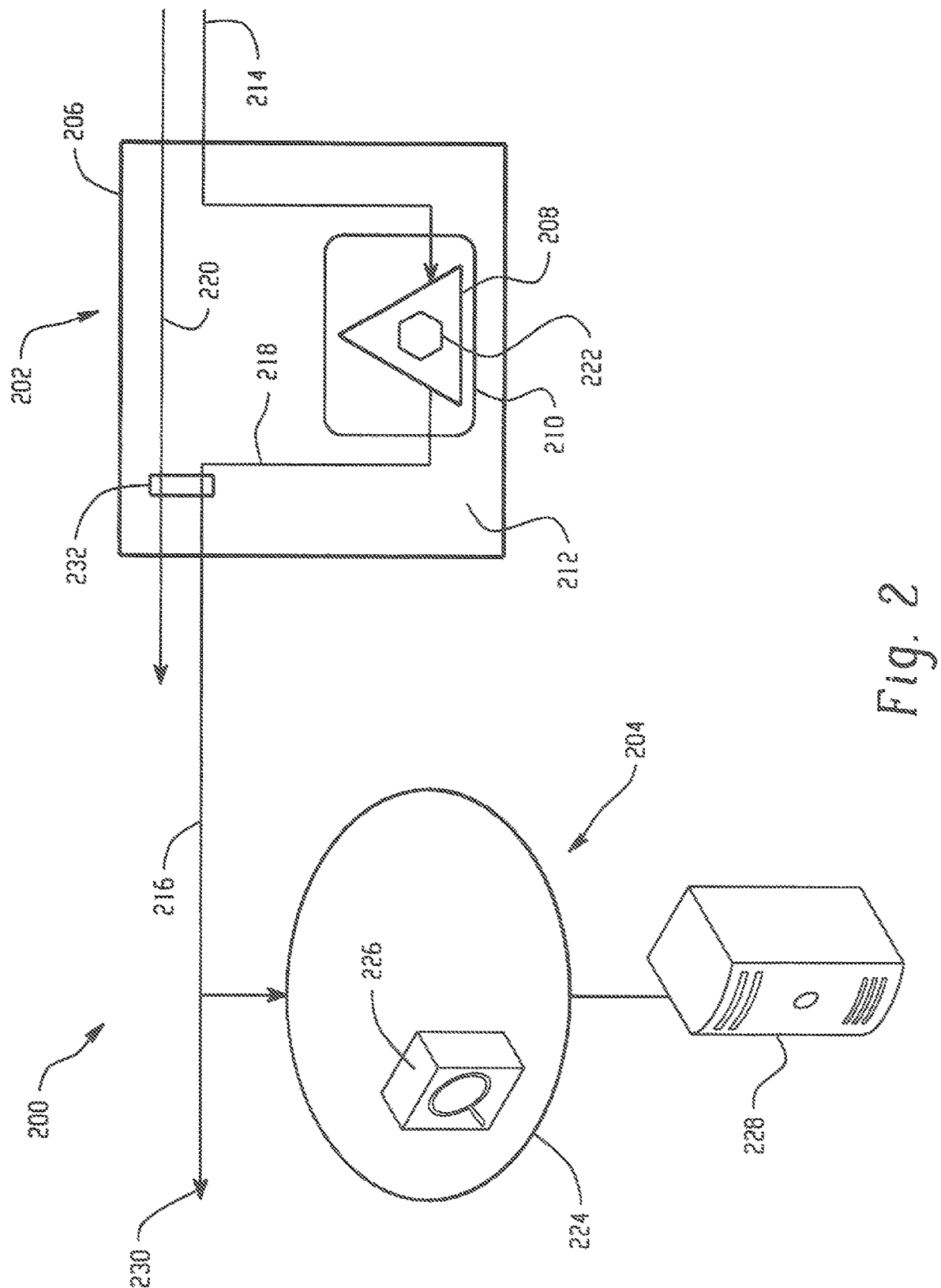
FIG. 2 shows a diagram of a system for analyzing of surface acidity of a sample having a low surface area, in accordance with some embodiments.

According to some embodiments, FIG. 2 shows a diagram of a system 200 for analyzing of surface acidity of a sample having a low surface area. In some embodiments, the system 200 for providing quantification of surface acidity of a sample includes a TPD system 202 and a MS system 204.

In some embodiments, the TPD system 202 includes a chemisorption analyzer 206, such as an Autochem II 2920 equipment. In some embodiments the TPD system 202 includes a reactor 208, such as a quartz reactor, where the sample 222 with a low surface area is placed. In some embodiments, the steps 110-150 of the process 100 in FIG. take place in the reactor 208. In some embodiments, the TPD system 202 includes a furnace 210 within a chamber 212 of the chemisorption analyzer 206. In some embodiments, the furnace 210 can be used to heat the sample reactor 208 and the sample. In some embodiments, the furnace 210 can operate in a temperature range from room temperature to 1500° C. The reactor 208 is placed into the furnace 210. In some embodiments, the chemisorption analyzer 206 can perform TPD. In some embodiments, the chemisorption analyzer 206 can also allow sample gases 218 to flow through the surface area of the sample via the reactor 208. In some embodiments, the chemisorption analyzer 206 can also allow sample gases 218 to flow through the reactor 208 through one or more inlets 214 and one or more outlets 216.

In some embodiments, the chemisorption analyzer 206 can detect the volume of the gas flowing through the sample reactor 208 using a method, such as the thermal conductivity difference measurement, by a thermal conductivity detector (TCD) 232, between the sample gases 218 and a reference gas 220.

In some embodiments, the MS system 204 includes a Mass Spectrometer 224 coupled to the TPD system 202 through a gas outlet 216. In some embodiments, the TPD system 202 and the MS system 204 operate substantially simultaneously.

In some embodiments, the Mass Spectrometer 224 is a Quadrupole Mass Spectrometer. In some embodiments, a filter system of the Quadrupole Mass Spectrometer creates a radio frequency (RF) quadrupole oscillating electrical field by four parallel rods arranged in the form of a square. The electrical field selectively stabilizes or destabilizes the paths of ions passing through the field between the four parallel rods. The potentials on the four rods can be changed continuously or discretely to allow ions in a certain range of mass/charge ratio (m/z) to pass through the system.

In some embodiments, the Quadrupole Mass Spectrometer 224 is equipped with one or more SEM detectors 226. In some embodiments, the Quadrupole Mass Spectrometer 224 is equipped with a faraday detector (not shown in FIG. 2). In some embodiments, the combination of Quadrupole Mass Spectrometer 224 with an SEM detector 226 can improve the performance of the MS 204 in terms of sensitivity and selectivity compared with conventional methods and systems. For example, in some conventional methods, a thermal conductivity detector (TCD) is used to measure the quantity of the probe molecules, which leads to low resolution and inaccuracy.

In some embodiments, the gas released in step 140 in FIG. 1 from the TPD system 202 containing the probe molecules is ionized by the MS system 204. In some embodiments, the gas is ionized by bombarding the gas with electrons. In some embodiments, the gas molecules are broken into charge fragments. In some embodiments, those ions were separated by their mass-to charge ratio (m/z) and detected by the SEM detectors 226.

In some embodiments, the MS system 204 is further controlled by a computer 228 that monitors the effluent gas from the TPD system 202 in step 140 of FIG. 1. In some embodiments, the computer 228 analyzes the results of the MS system 204 automatically.

In some embodiments, the desorbed probe molecules from the TPD system 204 in step 140 are ionized and measured by the MS system 204. In some embodiments, the MS system 204 can report a relative abundance of detected ions of each species in the gas from the TPD system 204 in step 140 as a function of a mass to charge ratio (m/z).

In some embodiments, the result signals obtained from MS system 204 are then calibrated and converted into the concentration profile and/or temperature profile of the probe molecule as a function of time recorded from the start of the TPD process of step 140 in the TPD system 204. In some embodiments, the remaining gas from the TPD system 202 and MS system 204 is removed through a vent 230 connected to both of the TPD system 202 and MS system 204.

Many different aspects and embodiments are possible. After reading this specification, those skilled in the art will appreciate that these aspects and embodiments are only illustrative and do not limit the scope of the present invention. Embodiments may be in accordance with any one or more of the items as disclosed herein.

EXAMPLE

Example 1: A method and system of surface acidity quantification on a low surface area sample according to an embodiment described herein were used to characterize the surface acidity of an example having a low surface area to mass ratio.

Figure 3:
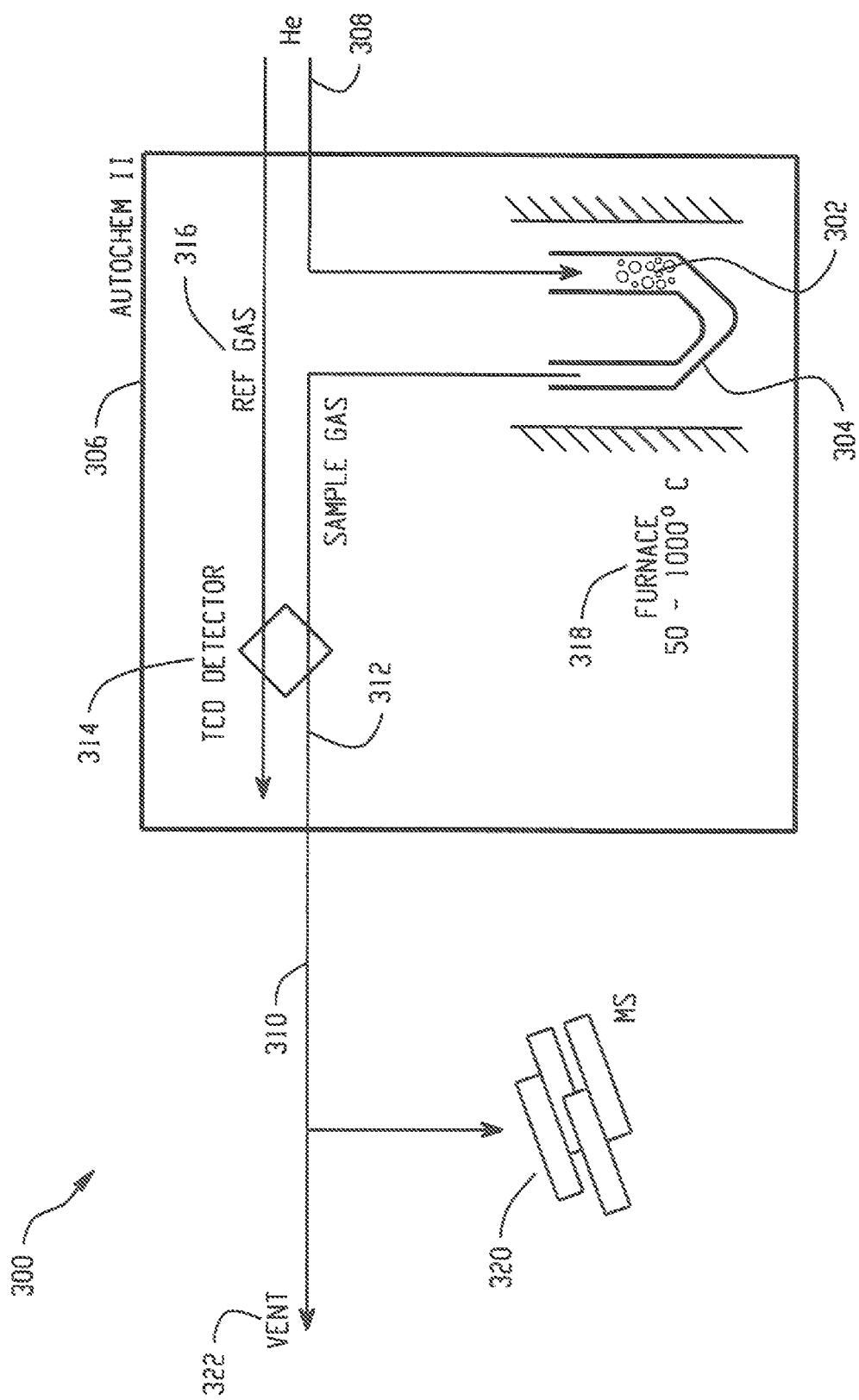
FIG. 3 shows a diagram of an exemplary experimental setup for the method and system of surface acidity quantification on a low surface area.

FIG. 3 shows a diagram 300 of an experimental setup for the method and system of surface acidity quantification on a low surface area according the example 1. A sample alumina catalyst carrier 302 was provided for this process. The low surface area alumina catalyst carrier 302 had a surface area to mass ratio of 0.77 $m^2/g$ and a weight of 5.7 g. The total surface area of the alumina catalyst carrier 302 was 4.40 $m^2$. The alumina sample 302 was crushed and loaded into a quartz reactor 304. The quartz reactor was situated in the furnace of a fully automated chemisorption analyzer 306. In this experiment, an Autochem II 2920 by Micromeritics was used as the chemisorption analyzer 306. The chemisorption analyzer 306 can perform temperature-programmed desorption (TPD). A thermal conductivity detector (TCD) 314 within the Autochem II 2920 equipment 306 chamber was used to detect the volume of sample gas 312 flowing through the sample reactor 304 from the thermal conductivity difference between the sample gas 312 and a reference gas 316. A furnace 318 within the Autochem II 2920 equipment 306 chamber was utilized to heat a quartz reactor 304 and the sample 302.

A pretreatment step was performed to remove surface moisture from the alumina sample 302. The purpose of pretreatment is to reduce an interference of other chemical such as water on the sample 302 during the subsequent adsorption and desorption steps. According to signals from MS, the pretreatment conditions can be optimized to achieve an acceptable signal to noise ratio, for example, a signal to noise ratio of greater than 100:1. During the pretreatment step, the alumina sample 302 was heated within the furnace 318 and the temperature was maintained at about 500° C. for about 15 to 30 minutes within a Helium or Argon gas flow. The heating elevation rate was about 6-10° C./min from about 50° C. to about 500° C. The Helium or Argon gas flowed into the sample reactor 304 through an inlet 308 and out of the sample reactor 304 through an outlet 310. The flow rate of the Helium or Argon gas was about 25 $cm^3$/minute.

An adoption step was performed after the pretreatment step. In the adsorption step, a probe molecule Ammonia or NH3 was chosen based on the composition and the catalytic application of the alumina sample 302. During the adsorption step, the alumina sample 302 was heated within the furnace 318 and the temperature was maintained at about 50-180° C. for about 15 minutes within a Helium gas or Argon gas flow mixed with 5% of ammonia gas by volume. The Helium and ammonia gas mixture flowed into the sample reactor 304 through an inlet 308 and out of the sample reactor 304 through an outlet 310. The flow rate of gas mixture was about 15 $cm^3$/minute. During a chemical adsorption process, chemical bonds between the probe molecule gas and certain solid surfaces of the sample 302 are formed. The chemical adsorption stops when probe molecule no longer has adequate contact directly with the surface of the sample 302 sufficient to form the chemical bond. Physical adsorption can also take place on all surfaces of the sample 302 and can form layers beyond the single layer of chemical adsorption.

A flushing step was performed after the adsorption step. In this experiment, only chemically adsorbed ammonia probe molecules were useful in the analysis of determining active sites of the surface area of sample 302. Acid sites bond with NH3 probe molecules. By removing physically adsorbed NH3 probe molecules that do not bond with acid sites, an accurate assessment of the number of acid sites on the surface area of sample 302 can be obtained during the subsequent desorption step. During the flushing step, the alumina sample 302 was heated within the furnace 318 and the temperature was maintained at about 50-180° C. for about 60 to 120 minutes within a Helium or Argon gas flow. The Helium or Argon gas flowed into the sample reactor 304 through an inlet 308 and out of the sample reactor 304 through an outlet 310. The flow rate of the Helium or Argon gas was about 25-50 $cm^3$/minute. The flushing step removed the physically adsorbed ammonia probe molecules from the surface of the alumina sample 302.

A TPD step was performed after the flushing step. During the TPD, the temperature for heating the alumina sample 302 within the furnace 318 was increased linearly with time from an initial temperature of 50° C. to about 500-900° C. in a controlled manner. The heating elevation rate was about 6-10° C./min from the initial temperature of 50° C. The heating was within a Helium or Argon gas flow. The temperature at about 500-900° C. was maintained for about 15 to 30 minutes. The Helium or Argon gas flowed into the sample reactor 304 through an inlet 308 and out of the sample reactor 304 through an outlet 310. The flow rate of the Helium or Argon gas was about 25 cm$^3$/minute. The chemically adsorbed ammonia probe molecules were released from the surface area of sample 302 and turned back to their gas phase.

A Mass Spectroscopy (MS) 320 was coupled to the TPD experiment apparatus including the Autochem II 2920 equipment 306. In this example, the MS 320 used was a Quadrupole Mass Spectrometer. The filter system of the Quadrupole Mass Spectrometer creates a radio frequency (RF) quadrupole oscillating electrical field by four parallel rods arranged in the form of a square. The electrical field selectively stabilizes or destabilizes the paths of ions passing through the field between the four parallel rods. The potentials on the four rods can be changed continuously or discretely to allow ions in a certain range of mass/charge ratio (m/z) to pass through the system. Additionally, the Quadrupole Mass Spectrometer was equipped with an SEM detector. The combination of Quadrupole Mass Spectrometer with an SEM detector can improve the performance of the MS 320 in terms of sensitivity and selectivity compared with conventional methods and systems. The sample gas 312 was ionized by the MS 320 by bombarding the gas with electrons. The sample gas 312 molecules were broken into charge fragments. Those ions were separated by their mass-to charge ratio and detected by the SEM detectors.

The MS 320 was further controlled by a computer that monitored the effluent gas from the TPD process and analyzed the results. The desorbed ammonia probe molecules from the TPD apparatus (Autochem II 2920) were ionized and measured by the MS 320. The MS 320 reported a relative abundance of detected ions of each species in the sample gas 312 as a function of a mass to charge ratio (m/z). The result signals obtained from MS 320 were then calibrated and converted into NH3 concentration profile and temperature profile as a function of time during the TPD step. The remaining gas from the TPD and MS system was removed through a vent 322.

Figure 4:
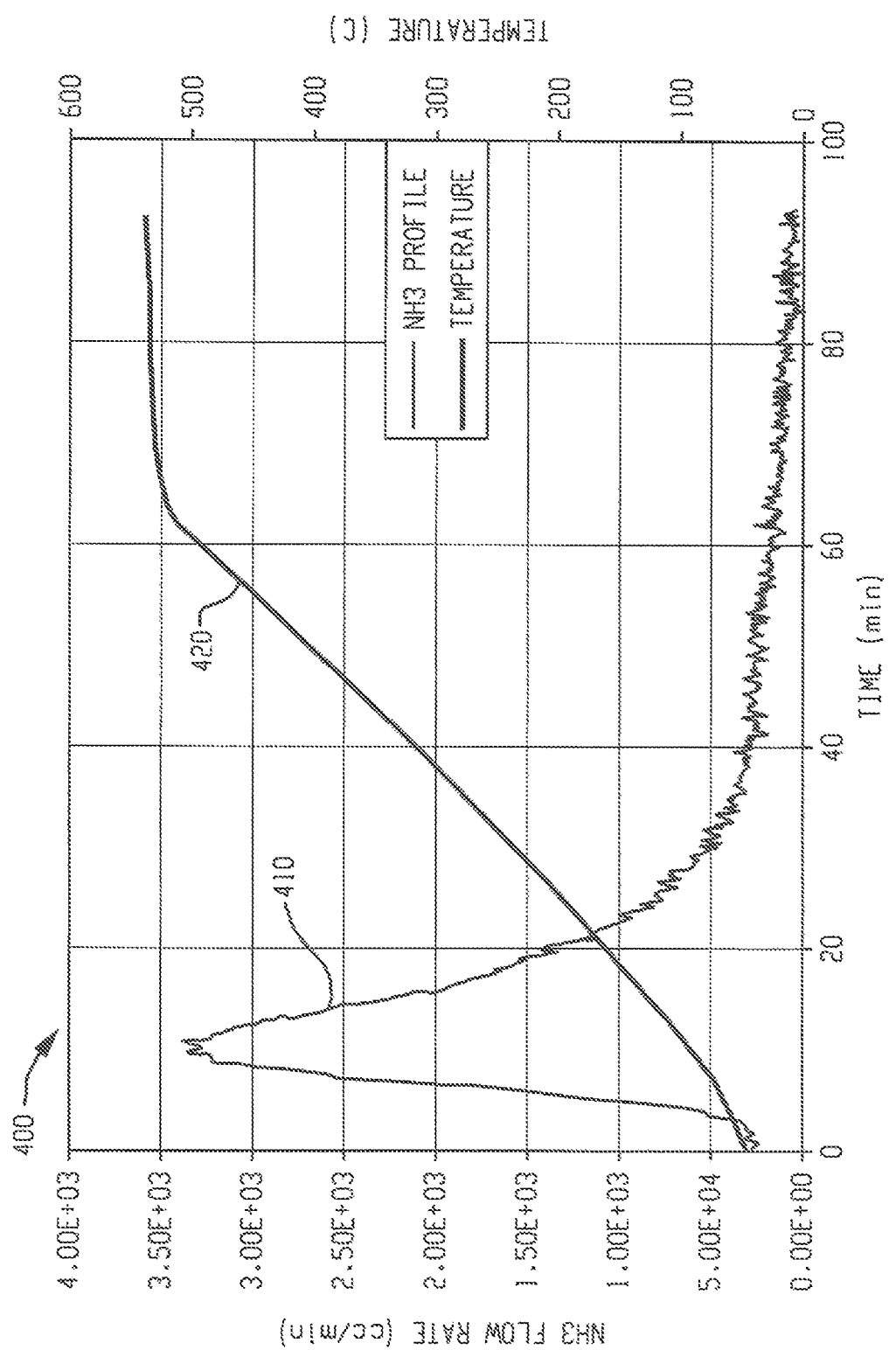
FIG. 4 shows an exemplary NH3 desorption profile and a temperature profile as a function of desorption time during the temperature-programmed desorption (TPD) process.

FIG. 4 shows a NH3 desorption profile 410 and a temperature profile 420 as a function of desorption time during the TPD process of this experiment on chart 400. The x-axis of the chart 400 represents desorption time during the TPD step. The Y-axis on the left side of the chart 400 represents NH3 gas flow rate in cm$^3$/min. The Y-axis on the right side of the chart 400 represents actual temperature in ° C. during the TPD process. From the NH3 desorption profile 410 and the temperature profile 420, the effluent NH3 flow rate from TPD initially increased as the temperature increased. The effluent NH3 flow rate reached to a peak at $3.4\times10^{-3}$ cm$^3$/min in about 10 minutes in the TPD process. Then the effluent NH3 flow rate started to decrease as the temperature continued to increase. After 60 minutes passed in the TPD process, the temperature stabilized at about 500° C. while the effluent NH3 flow rate decreased to a negligible level of below $5\times10^{-4}$ cm$^3$/min. The NH3 desorption curve 410 was further integrated to obtain a total amount of NH3 adsorption from the low surface of the sample 302. With known total surface area of the alumina sample 302, the surface acidity site density can be calculated to characterize the surface acidity of the sample 302.

In the foregoing, reference to specific embodiments and the connections of certain components is illustrative. It will be appreciated that reference to components as being coupled or connected is intended to disclose either direct connection between said components or indirect connection through one or more intervening components as will be appreciated to carry out the methods as discussed herein. As such, the above-disclosed subject matter is to be considered illustrative, and not restrictive, and the appended claims are intended to cover all such modifications, enhancements, and other embodiments, which fall within the true scope of the present invention. Thus, to the maximum extent allowed by law, the scope of the present invention is to be determined by the broadest permissible interpretation of the following claims and their equivalents, and shall not be restricted or limited by the foregoing detailed description. The embodiments were chosen and described in order to best explain principles of operation and practical applications, to thereby enable others skilled in the art.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus.

As used herein, and unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

It will be understood that, although the terms "first," "second," etc. may be used herein to describe various elements, these elements should not be limited by these terms. These terms are only used to distinguish one element from another.

The Abstract of the Disclosure is provided to comply with Patent Law and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all features of any of the disclosed embodiments. Thus, the following claims are incorporated into the Detailed Description, with each claim standing on its own as defining separately claimed subject matter.

What is claimed is:

1. A method of quantification of surface acidity of a sample, the method comprising the steps of:
   (1) removing surface moisture of the sample using a pretreatment process comprising:
   heating the sample at about 6-10° C./min, from an initial temperature of about 50-100° C. to about 500-600° C., and
   maintaining a temperature of the sample of about 500-600° C. for about 15 to 30 minutes, wherein the sample is within a Helium or Argon gas flow at a flow rate of about 20-50 cm³/minute;
(2) adsorbing a molecular probe on a surface of the sample comprising:
maintaining a temperature of the sample of about 50-180° C. for about 10 to 20 minutes within a Helium or Argon gas mixed with 5% of the molecular probe flowing at a flow rate of about 10-50 cm³/minute;
(3) removing physically adsorbed molecular probe from the surface of the sample comprising:
maintaining a temperature of the sample of about 50-180° C. for about 60 to 120 minutes within a Helium or Argon gas flow at a flow rate of about 25-50 cm³/minute;
(4) releasing the physically adsorbed molecular probe by a method that includes a temperature programmed desorption (TPD) process comprising:
heating the sample with the molecular probe adsorption at about 6-10° C./min, from an initial temperature of about 50-100° C. to about 500-900° C., and
maintaining a temperature of the sample of about 500-900° C. for about 15 to 30 minutes,
wherein the sample is within a Helium or Argon gas flow at a flow rate of about 20-50 cm³/minute; and
(5) measuring a total amount of the molecular probe physically desorbed from the TPD process by a method that includes mass spectroscopy (MS),
wherein the sample has a surface area to mass ratio of less than 5 m²/g.

2. The method of claim 1, wherein the surface area to mass ratio is less than 1 m²/g.

3. The method of claim 1, wherein the sample has a total surface area of at least 3 m².

4. The method of claim 3, wherein the sample has a total surface area of not greater than 25 m².

5. The method of claim 1, wherein the sample comprises a catalyst carrier.

6. The method of claim 1, wherein the sample comprises a ceramic material.

7. The method of claim 1, wherein the sample comprises alumina, zirconia, titania, silica, zeolite, or a combination thereof.

8. The method of claim 1, wherein the molecular probe is $NH_3$.

9. The method of claim 1, wherein the molecular probe comprises Pyridine or other alkaline molecule.

10. The method of claim 1, wherein the MS method comprises using Quadrupole Mass Spectrometers.

11. The method of claim 10, wherein the MS method comprises using a secondary electron multiplier detector.

* * * * *